US00PP23741P3

(12) United States Plant Patent
Bradford

(10) Patent No.: US PP23,741 P3
(45) Date of Patent: Jul. 16, 2013

(54) INTERSPECIFIC TREE NAMED 'PLUMRED VIII'

(50) Latin Name: ***Prunus* sp.**
Varietal Denomination: Plumred VIII

(76) Inventor: Lowell Glen Bradford, Le Grand, CA (US)

( * ) Notice: Subject to any disclaimer, the term of this patent is extended or adjusted under 35 U.S.C. 154(b) by 69 days.

(21) Appl. No.: 13/374,023

(22) Filed: Dec. 8, 2011

(65) Prior Publication Data

US 2013/0152245 P1 Jun. 13, 2013

(51) Int. Cl.
*A01H 5/00* (2006.01)

(52) U.S. Cl.
USPC ..... Plt./180

(58) Field of Classification Search
USPC ..... Plt./180
See application file for complete search history.

(56) References Cited

U.S. PATENT DOCUMENTS

PP20,863 P2 3/2010 Bradford

*Primary Examiner* — Annette Para

(57) ABSTRACT

The present invention relates to an interspecific tree and more particularly to a new and distinct variety broadly characterized by a medium size, vigorous, hardy, and productive tree. Being self-unfruitful, the present variety requires cross pollination from an apricot, interspecific, or plum that blooms during the mid to late season. The present variety produces a moderately heavy bloom, but is pollen deficient and should have pollinators grafted in the center of the tree to entice good bee activity for sufficient pollination. The fruit matures under the ecological conditions described during mid August, with first picking on Aug. 19, 2011. The fruit is uniformly medium to large in size, deep red in skin color, clingstone in type, globose in shape, nearly full red in flesh color, firm and crisp in texture, and excellent in flavor.

1 Drawing Sheet

Botanical classification: *Prunus* sp.
Varietal denomination: 'PLUMRED VIII'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree which has been denominated varietally as 'Plumred VIII'.

During a typical blooming season I isolate as seed parents both individual and groups of different plum trees by covering them with screen houses. A hive of bees is placed inside each such house, and bouquets to provide pollen from different plum, apricot, and interspecific hybrid trees are placed in buckets near the trees approximately every two days for the duration of the bloom. During 2001 one such house containing an unpatented red plum, code named '19P442', was crossed by me in this manner. To pollinate this red plum, I selected bouquets from several sources of apricot and interspecific hybrid trees without keeping specific written details. Upon reaching maturity the fruit from this red plum tree was harvested and the seeds were removed, cracked, stratified and germinated as a group with the label "H8A". They were grown as seedlings on their own root in my greenhouse and upon reaching dormancy transplanted to a cultivated area of my experimental orchard located near Le Grand, Calif. in Merced County (San Joaquin Valley). During the summer of 2005 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, '19P442' (unpatented) plum, by being self-unfruitful and by producing fruit that is full red in flesh color, globose in shape, and dark red to purple in skin color, but is distinguished therefrom by producing fruit that is much larger in size and that matures about fifty days later.

The present variety is most similar to its sister, 'Blackred VIII' (U.S. Plant Pat. No. 20,863) interspecific, by being self-unfruitful and by producing fruit that is similar in size, clingstone in type, and firm in texture, but is distinguished therefrom by being pollen deficient and producing fruit that is darker red in flesh color, that is deep red instead of black in skin color, that is globose instead of oblate in shape, and that matures about eight days earlier.

SUMMARY OF VARIETY

The present interspecific variety is characterized by a medium size, vigorous, hardy, and productive tree. Being self-unfruitful, the present variety requires cross pollination from an apricot, interspecific, or plum that blooms during the mid to late season. The present variety produces a moderately heavy bloom, but is pollen deficient and should have pollinators grafted in the center of the tree to entice good bee activity for sufficient pollination. The fruit matures under the ecological conditions described during mid August, with first picking on Aug. 19, 2011. The fruit is uniformly medium to large in size, deep red in skin color, clingstone in type, globose in shape, nearly full red in flesh color, firm and crisp in texture, and excellent in flavor.

DRAWING

The accompanying photograph consists of four whole fruits positioned to display the characteristics of the skin color and form, one fruit divided to reveal the flesh and stone, a young tip shoot growth, typical leaves, and three insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Aug. 24, 2011, on the original tree during its tenth growing season. The flower and bud descriptions were developed during the previous blooming season. All major color code designations are by reference to the Inter-Society Color Council, National Bureau of Standards. Common color names are also used occasionally.

PARENTAGE

Seed parent: '19P442' plum (unpatented).
Pollen parent: Unknown.

TREE

Size: Medium, reaching a height of 10' [3.05 m.] and a spread of 6' [1.83 m.] after ten growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Central leader.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-unfruitful, requiring cross pollination by a suitable late seasonal blooming apricot, interspecific, or plum, such as 'Plumsweet IV' (U.S. Plant Pat. No. 16,461) interspecific tree.

Bearing: Regular so far, no crop failures observed, weather dependent.

Trunk:

- *Size*.—Medium, reaching a maximum diameter of 4¾" [120.7 mm.] after the tenth growing season.
- *Texture*.—Medium shaggy.
- *Bark color*.—A Dark grayish brown [62. d.gy.Br] and Dark brown [59. d.Br] variegation.
- *Lenticels*.—Approximate Number Per Square Inch: 7. Color: Light orange [52. l.O]. Size: ¼" [6.4 mm.] to ½" [12.7 mm.]. Shape: Elongated, eye-shaped.

Branches:

- *Size*.—Diameter of the central leader is 4¼" [108 mm.] measured 12" above the first hanger, maximum diameter of first hanger is ¾" [19.1 mm.].
- *Texture*.—Smooth on first year wood, increasing roughness with age.
- *Color*.—1st Year Wood Topside: Grayish red [19. gy.R]. 1st Year Wood Underside: Brilliant yellow green [116. brill.YG]. 2nd Year Wood: Strong brown [55. s.Br] with Strong yellow green [117. s.YG] permeating through from underneath.
- *Lenticels*.—Number Per Square Inch: About 40 on second year wood. Color: Light yellowish brown [76. l.yBr]. Size: 1/16" [1.6 mm.]. Shape: Eye-shaped.

Leaves:

- *Size*.—Medium to Large. Average Length: 4½" [114.3 mm.]. Average Width: 2⅛" [54 mm.].
- *Arrangement*.—Alternate.
- *Thickness*.—Medium.
- *Form*.—Elliptical.
- *Apex*.—Acuminate.
- *Base*.—Acute with an average angle base angle of 70 degrees.
- *Surface*.—Smooth.
- *Color*.—Dorsal Surface: Moderate olive green [125. m.OlG]. Ventral Surface: Moderate yellow green [120. m.YG].
- *Margin*.—Finely serrate.
- *Venation*.—Pinnately net veined.
- *Petiole*.—Average Length: ⅝" [15.9 mm.]. Average Thickness: 1/16" [1.6 mm.]. Color: Brilliant yellow green [116. brill.YG], often Deep pink [3. deep Pk] where exposed to direct sunlight.
- *Stipules*.—Number: Usually 2 per leaf, up to 6 per growing tip. Average Length: ⅜" [9.5 mm.]. Color: Moderate yellow green [120. m.YG] becoming Deep yellowish brown [75. deep yBr] with age.
- *Glands*.—Number: Mostly 2 per leaf. Position: Alternately positioned at the intersection of the petiole and the leaf blade. Size: Small. Form: Globose. Color: Light yellow green [119. l.YG] becoming Grayish reddish brown [46. gy.rBr] with age. Leaf buds: Pointed, medium.

Flower buds:

- *Hardiness*.—Hardy, with respect to central California winters.
- *Diameter*.—Typically 3/16" [4.8 mm.] 1 week before bloom.
- *Length*.—Typically ⅜" [9.5 mm.] 1 week before bloom.
- *Form*.—Not appressed.
- *Surface*.—Pubescent.
- *Tip color*.—White [263. White].

Flowers: Perfect, complete, perigynous, usually a single pistil, typically thirty or more stamens, five sepals and petal locations alternately positioned.

- *Average flower diameter*.—1 1/16" [27.0 mm.].
- *Number of petals*.—Five, no double blossoms observed.
- *Petal shape*.—Oval to circular.
- *Petal margin*.—Entire, slightly wavy.
- *Average petal diameter*.—½" [12.7 mm.].
- *Average petal length*.—9/16" [14.3 mm.].
- *Petal apex*.—Rounded.
- *Petal base*.—Obtuse.
- *Petal color*.—White [263. White] on both sides.
- *Anther color*.—Yellowish White [92. yWhite].

*Stigma color*.—Light greenish yellow [101. l.gY].
*Sepal color*.—Light yellow green [119. l.YG] on the outer surface.
*Sepal length*.—7/32" [5.6 mm.].
*Sepal width*.—3/16" [4.8 mm.].
*Sepal apex*.—Rounded to elliptical to match the width and length.
*Sepal margin*.—Fairly smooth to the naked eye, slightly serrated when magnified.
*Average pistil length*.—11/16" [17.5 mm.].
*Average stamen length*.—7/16" [11.1 mm.].
*Fragrance*.—Moderate.
*Pollen production*.—Deficient.
*Blooming period*.—Medium to late, one day before 'Santa Rosa' plum (unpatented).
*Onset of bloom*.—One percent on Mar. 3, 2011.
*Date of full bloom*.—Mar. 10, 2011.
*Duration of bloom*.—One to two weeks, dependent on ambient temperature.
*Bloom density*.—Moderate.
*Number per cluster*.—2 to 10, average 5.

FRUIT

Maturity when described: Firm ripe, Aug. 24, 2011.
Date of first picking: Aug. 19, 2011.
Date of last picking: Sep. 2, 2011.
Size: Uniform, medium to large.
*Average diameter axially*.—2 9/16" [65.1 mm.].
*Average diameter across cheek plane*.—2¾" [69.9 mm.].
*Average diameter across suture plane*.—2¾" [69.9 mm.].
*Typical weight*.—6.2 ounces [175.8 grams].
Form: Globose, mostly symmetrical.
*Longitudinal section form*.—Round.
*Transverse section through diameter*.—Round.
Suture: An inconspicuous Very dark purplish red [260. v.d.pR] line located in a very shallow groove extending from the base to the pistil point.
Ventral surface: Rounded, lipped near the shoulders.
Lips: Equal.
Cavity: Flaring, circular, suture showing on one side.
*Depth*.—7/16" [11.1 mm.].
*Breadth*.—1 1/16" [27 mm.].
Base: Truncate, slightly cordate if viewed parallel to the suture.
Apex: Rounded.
Pistil point: A conspicuous Strong yellowish brown [74. s.yBr] dot located at the end of the suture.
Stem: Medium.
*Average length*.—⅜" [9.5 mm.].
*Average width*.—1/16" [1.6 mm.].
Skin:
*Thickness*.—Medium.
*Surface*.—Smooth.
*Tenacity*.—Tenacious to the flesh.
*Astringency*.—Slight.
*Tendency to crack*.—Slight, more prone when the shoulder is in contact with the limb.
*Color*.—Very deep red [14. v.deep R] over a Deep red [13. deep R] background with Strong yellowish brown [74. s.yBr] freckling throughout.
*Bloom*.—Moderate.
Flesh:
*Color*.—Dark red [16. d.R] near the skin and stone with Dark pink [6. d.Pk] in the middle.
*Surface of pit cavity*.—Covered with Dark red [16. d.R] broken fibers when twisted away from stone.
*Amygdalin*.—Moderate.
*Juice*.—Abundant, rich.
*Texture*.—Firm, crisp.
*Fibers*.—Abundant, fine, tough.
*Ripens*.—Somewhat earliest at apex.
*Flavor*.—An excellent balance of acid and sugar, typically 20 brix.
*Aroma*.—Slight.
*Eating quality*.—Excellent.

STONE

Type: Clingstone.
Form: Oval.
Hilum: Narrow, oblong.
Base: Straight.
Apex: Acute with an average angle of 80 degrees.
Sides: Equal.
Surface: Rough throughout with a groove on each side of the dorsal fin.
External color of stone: Strong yellowish brown [74. s.yBr] when first removed.
Pit wall color when cracked: Light yellowish brown [76. l.yBr].
Cavity surface color: A Strong yellowish brown [74. s.yBr] and Moderate yellowish brown [77. m.yBr] two-tone.
Average pit wall thickness: 1/16" [1.6 mm.].
Average width: 9/16" [14.3 mm.].
Average length: ⅞" [22.2 mm.].
Average breadth: ⅜" [9.5 mm.].
Tendency to split: Slight.
Kernel:
*Form*.—Oval.
*Skin color*.—Brownish orange [54. brO] when first removed.
*Pellicle color*.—Light grayish brown [60. l.gy.Br].
*Vein color*.—Light grayish brown [60. l.gy.Br].
*Taste*.—Bitter.
*Viable*.—Yes.
*Average width*.—⅜" [9.5 mm.].
*Average length*.—9/16" [14.3 mm.].
*Amygdalin*.—Moderate.

USE

Market: Fresh market and long distance shipping.
Keeping quality: Good, fruit quality observed to remain in good condition after 30 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to its sister, 'Blackred VIII' (U.S. Plant Pat. No. 20,863) interspecific, by being self-unfruitful and by producing fruit that is similar in size, clingstone in type, and firm in texture, but is distinguished therefrom by being pollen deficient and producing fruit that is darker red in flesh color, that is deep red instead of black in skin color, that is globose instead of oblate in shape, and that matures about eight days earlier.

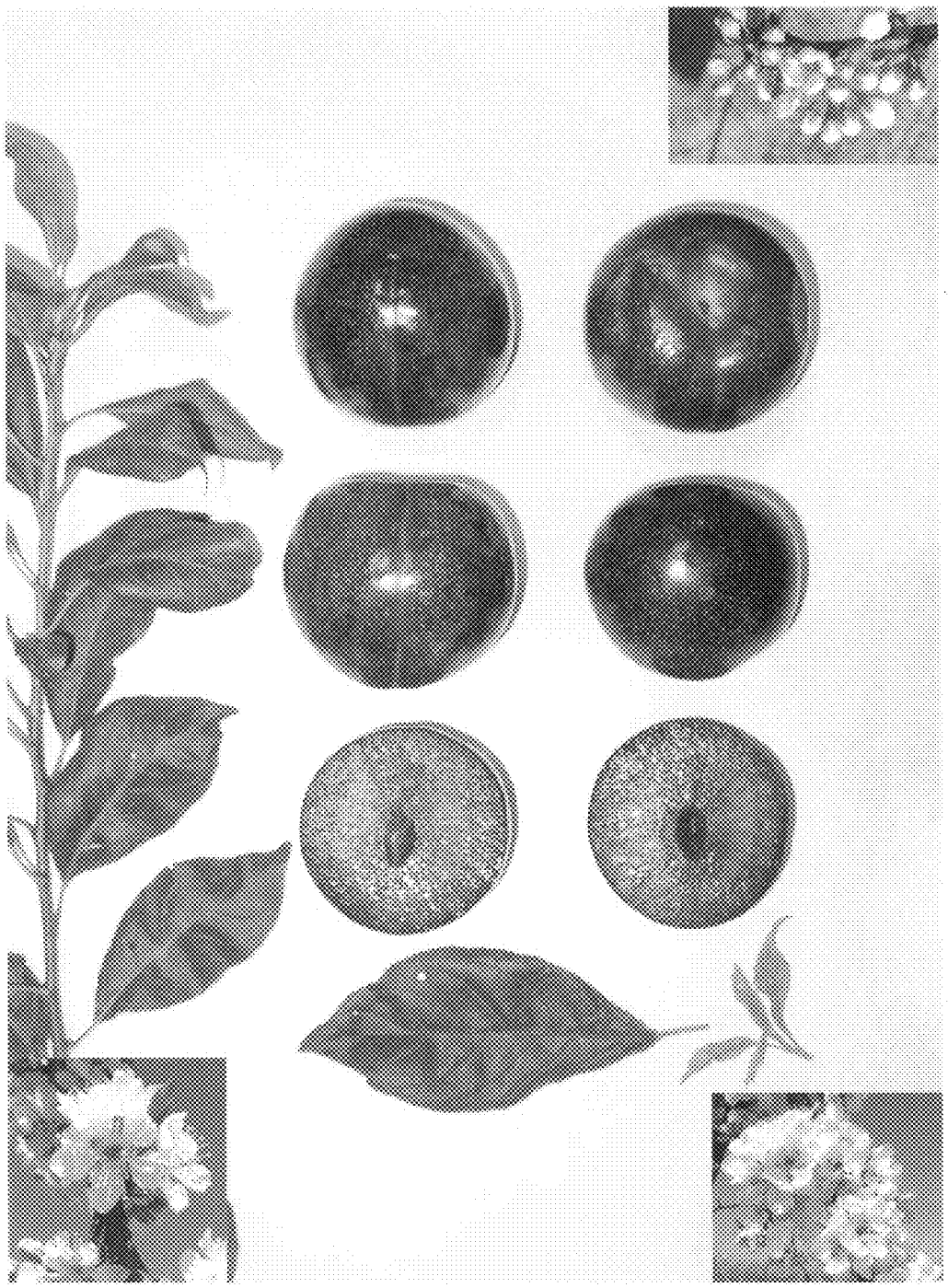

* * * * *